US012760670B2

(12) United States Patent
Borsch et al.

(10) Patent No.: US 12,760,670 B2
(45) Date of Patent: Oct. 13, 2026

(54) METHOD AND DEVICE FOR DETERMINING THE ENGINE OIL QUALITY OF AN INTERNAL COMBUSTION ENGINE

(71) Applicant: Vitesco Technologies GmbH, Regensburg (DE)

(72) Inventors: Patrick Borsch, Obertraubling (DE); Karl Gruenbeck, Kelheim (DE)

(73) Assignee: VITESCO TECHNOLOGIES GMBH, Regensburg (DE)

( * ) Notice: Subject to any disclaimer, the term of this patent is extended or adjusted under 35 U.S.C. 154(b) by 390 days.

(21) Appl. No.: 17/651,849

(22) Filed: Feb. 21, 2022

(65) Prior Publication Data

US 2022/0186641 A1 Jun. 16, 2022

Related U.S. Application Data

(63) Continuation of application No. PCT/EP2020/073755, filed on Aug. 25, 2020.

(30) Foreign Application Priority Data

Aug. 30, 2019 (DE) ..................... 10 2019 213 123.9

(51) Int. Cl.
*F01M 11/10* (2006.01)
*G01N 33/28* (2006.01)

(52) U.S. Cl.
CPC ......... *F01M 11/10* (2013.01); *G01N 33/2888* (2013.01); *F01M 2011/1446* (2013.01); *F01M 2011/1453* (2013.01); *F01M 2011/148* (2013.01); *F01M 2250/00* (2013.01); *F16N 2200/00* (2013.01)

(58) Field of Classification Search
CPC ............... F01M 11/10; F01M 2250/00; F01M 2011/1446; F01M 2011/1453; F01M 2011/148; G01N 33/2888; F16N 2200/00
See application file for complete search history.

(56) References Cited

U.S. PATENT DOCUMENTS

2003/0196479 A1 10/2003 Kasen
2004/0211246 A1 10/2004 Han et al.
2010/0307230 A1 12/2010 Gilch
2012/0006289 A1 1/2012 Petz
2014/0174408 A1 6/2014 Pfeiffer
(Continued)

FOREIGN PATENT DOCUMENTS

CN 103883375 A 6/2014
CN 110023599 A 7/2019
(Continued)

OTHER PUBLICATIONS

Chinese Office Action dated Nov. 27, 2023 for corresponding Patent Application No. 202080060873.5.
(Continued)

*Primary Examiner* — Peter J Macchiarolo
*Assistant Examiner* — John M Royston

(57) ABSTRACT

The disclosure provides a method and a device for determining the engine oil quality of an internal combustion engine. The engine oil quality is determined by evaluation of the switching times of an oil pressure switch of the internal combustion engine after a starting operation of the internal combustion engine.

20 Claims, 3 Drawing Sheets

(56) References Cited

U.S. PATENT DOCUMENTS

| | | | | |
|---|---|---|---|---|
| 2016/0069856 | A1* | 3/2016 | Gorritxategi ...... | G01N 15/0227<br>356/70 |
| 2019/0040775 | A1* | 2/2019 | Sarwar ..................... | F01M 1/02 |
| 2020/0063667 | A1 | 2/2020 | Lenk et al. | |

FOREIGN PATENT DOCUMENTS

| | | | |
|---|---|---|---|
| DE | 19901815 | A1 | 7/2000 |
| DE | 10053250 | A1 | 11/2002 |
| DE | 10311935 | A1 | 11/2003 |
| DE | 102006009910 | A1 | 9/2007 |
| DE | 102006038968 | A1 | 2/2008 |
| DE | 102006059071 | A1 | 6/2008 |
| DE | 102012004794 | A1 | 9/2013 |
| EP | 2388583 | A1 | 11/2011 |
| FR | 3002974 | A1 | 9/2014 |
| KR | 20030079541 | A | 10/2003 |
| KR | 20110033130 | A | 9/2012 |

OTHER PUBLICATIONS

Indian Examination Report dated May 2, 2022 for corresponding Indian Application No. 202217003356.

Indian Office Action dated Nov. 28, 2023 for corresponding Indian Patent Application No. 202217003356.

International Search Report and Written Opinion dated Dec. 10, 2020 from corresponding International Patent Application No. PCT/EP2020/073755.

German Office Action dated May 14, 2020 for corresponding German Patent Application No. 10 2019 213 123.9.

Korean Office Action dated Augurst 6, 2024 for corresponding Patent Application No. 10-2022-7010551.

Chinese Office Action dated Aug. 1, 2024 for corresponding Patent Application No. 202080060873.5.

* cited by examiner

METHOD AND DEVICE FOR DETERMINING THE ENGINE OIL QUALITY OF AN INTERNAL COMBUSTION ENGINE

CROSS-REFERENCE TO RELATED APPLICATIONS

This application claims the benefit of PCT Application PCT/EP2020/073755, filed Aug. 25, 2020 which claims priority to German Application DE 10 2019 213 123.9, filed Aug. 30, 2019. The disclosures of the above applications are incorporated herein by reference.

TECHNICAL FIELD

The disclosure relates to a method and a device for determining the engine oil quality of an internal combustion engine.

BACKGROUND

The engine oil of internal combustion engines ensures stable lubricity in all operating ranges of the internal combustion engine with the least possible friction of the moving mechanical components of the internal combustion engine.

In order to reduce fuel consumption and thus also the $CO_2$ emissions of internal combustion engines, it is known to lower the viscosity of the engine oil, which however reduces the lubricity of the engine oil. If fuel additionally enters into the engine oil, the lubricity of the engine oil can degrade to such an extent that engine damage occurs.

Even modern friction-optimized engine designs cause large fuel inputs into the engine oil via the piston rings, in particular during the warm-up phase of the internal combustion engine. These fuel inputs temporarily reduce the engine oil quality. An additional problem is an increase in the oil level caused by these fuel inputs. This can lead to foaming of the engine oil by the crankshaft of the internal combustion engine.

There is consequently a need to have permanent knowledge of the engine oil quality in order to resolve the conflict of aims between the lubricity of the engine oil and a reduction in friction without engine damage occurring.

It is already known to ascertain the quality of the engine oil using oil level sensors and/or special oil quality sensors. Here, resistive and capacitive measurement principles are used, where conclusions can be drawn regarding the chemical characteristics of the engine oil by way of resistance measurements, conductivity measurements or measurements of the dielectric constant.

An oil condition sensor device having an ultrasound sensor, a temperature sensor and an oil fill level sensor and an evaluation unit which derives oil condition variables from the output signals of the sensors mentioned, is known.

A known system for controlling the oil quality of internal combustion engines, where the oil quality is calculated by linking measured variables supplied by the engine. Here, the viscosity of the oil is ascertained from the rotational speed of the oil pump, the measured oil pressure and the oil temperature.

Another known method determines the oil quality in an oil feed line to an engine and/or a consumer. Here, at least one temperature and at least one pressure are measured in the oil feed line. Furthermore, at least one information item is generated from which a volume flow through the oil feed line is inferred. Information regarding the oil quality, in particular information regarding the viscosity of the oil, is ascertained from the measured temperature, the measured pressure and the volume flow.

SUMMARY

The disclosure provides a method and a device for determining the engine oil quality of an internal combustion engine, which can be implemented inexpensively and do not require any special oil quality sensors.

The method determines the engine oil quality of an internal combustion engine, where the engine oil quality is determined by an evaluation of switching times of an oil pressure switch of the internal combustion engine after a starting operation of the internal combustion engine.

Implementations of the disclosure may include one or more of the following optional features. In some implementations, the engine oil quality is determined by the evaluation of the switching times of the oil pressure switch of the internal combustion engine after a cold start of the internal combustion engine.

The engine oil quality may be determined by the evaluation of the switching times of the oil pressure switch of the internal combustion engine after a hot start of the internal combustion engine.

In some examples, the engine oil quality is determined in a manner dependent on the engine temperature prevailing upon the starting operation of the internal combustion engine.

The engine oil quality may be determined using a stored oil quality model.

In some examples, the engine oil quality is determined by a repeated evaluation of the switching times of the oil pressure switch.

In some implementations, short-term engine oil quality information is ascertained.

In some examples, long-term engine oil quality information is ascertained.

Changes in the viscosity of the engine oil may be ascertained.

In some examples, the ascertained oil quality information is compared with a further model.

In some implementations, the engine oil quality is ascertained during driving operation of the internal combustion engine using a targetedly effected change of an oil pressure setpoint value.

In some implementations, a device for determining the engine oil quality of an internal combustion engine is provided. The device has an engine controller and an oil pressure switch which, after a starting operation of the internal combustion engine, transmits binary switching information to the engine controller when a specified pressure threshold is exceeded. The engine controller is configured to determine the engine oil quality by evaluation of the switching times of the oil pressure switch.

The advantages of the disclosure are that the desired engine oil quality information is determined inexpensively without the use of a special oil quality sensor. In the described method, use is made of the fact that an analysis of the pressure gradient during the build-up of the engine oil pressure after a starting operation of the internal combustion engine allows conclusions to be drawn regarding the oil quality. Here, the pressure gradient is approximated using the switching times of an already existing oil pressure switch, which was hitherto merely used to signal to the engine controller, upon the exceedance of a specified engine oil pressure after a starting operation of the engine, that the engine has reached the minimum oil pressure required for engine operation.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
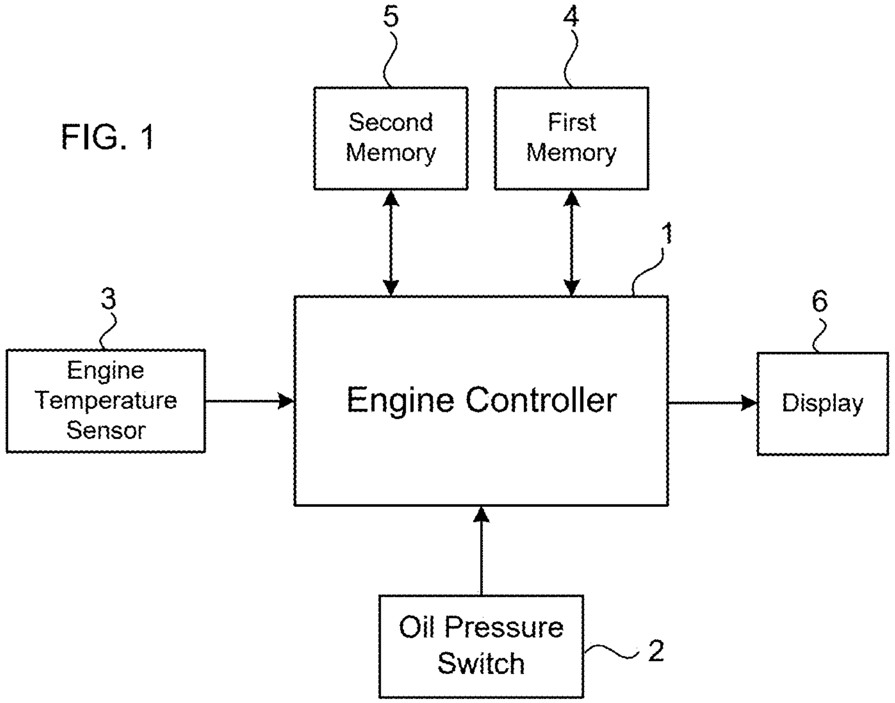
FIG. 1 is a block diagram of a device for determining the engine oil quality of an internal combustion engine.

FIG. 1 is a block diagram of a device for determining the engine oil quality of an internal combustion engine. The device has an engine controller 1, an oil pressure switch 2, an engine temperature sensor 3, a first memory 4, a second memory 5 and a display 6.

Output signals of the oil pressure switch 2 and of the engine temperature sensor 3, among others, are fed to the engine controller 1. Furthermore, the engine controller 1 controls the display 6 such that warning messages are displayed there, for example, as will be explained below. The engine controller 1 also communicates with the first and second memories 4 and 5. The first memory 4 stores data which correspond to an empirically ascertained oil quality model. The second memory 5 stores data corresponding to a further empirically ascertained model, for example a modeling of the fuel inputs in the engine oil based on the blow-by behavior and the outgassing when the engine operating temperature is reached.

The oil pressure switch 2 is arranged in the engine oil circuit and, after a starting operation of the internal combustion engine, the oil pressure switch 2 outputs binary switching information to the engine controller 1 when the engine oil pressure that builds up after the starting operation of the internal combustion engine exceeds a mechanically calibrated pressure threshold. This binary switching information is provided, for example, in the form of a transition from a high level to a low level, for example from level 1 to level 0. This binary switching information provided by the oil pressure switch has the task of signaling to the engine controller that the engine oil pressure that has built up after the starting operation of the internal combustion engine has reached the minimum oil pressure required for engine operation. The engine controller is furthermore configured to acquire the switching time of the oil pressure switch 2. The switching time of the oil pressure switch is understood here to mean the period of time that elapses from starting the engine until the outputting of the binary switching information by the oil pressure switch 2. Furthermore, the engine controller 1 is configured to determine the engine oil quality by evaluation of the switching times of the oil pressure switch. Use is made here of the fact that an analysis of the pressure gradient during the build-up of the engine oil pressure allows conclusions to be drawn regarding the engine oil quality, where the pressure gradient is approximated by the switching times of the oil pressure switch 2.

The aforementioned analysis of the pressure gradient can be used to determine information regarding the fuel input in the engine oil.

Furthermore, the viscosity of the engine oil changes over the service life of the engine oil and the engine operation of the internal combustion engine with fuel inputs into the engine oil. These viscosity differences are likewise manifest in the different response behavior of the oil pressure switch, that is to say in different switching times of the oil pressure switch.

After a starting operation of the internal combustion engine, the delivery of oil by a mechanical oil pump in the oil sump, and thus the build-up of pressure of the engine oil, is commenced. During the run-up of the engine, fluctuations in the oil pressure occur which are greater in the case of a cold start, in which the oil ducts are initially still empty, than during subsequent hot starts, in which the oil ducts are already filled. In both cases, however, based on the measurement and evaluation of the switching times of the oil pressure switch, it can be seen that large fuel inputs in the engine oil lead to shorter switching times of the oil pressure switch, as will be explained by way of example below.

Figure 2:
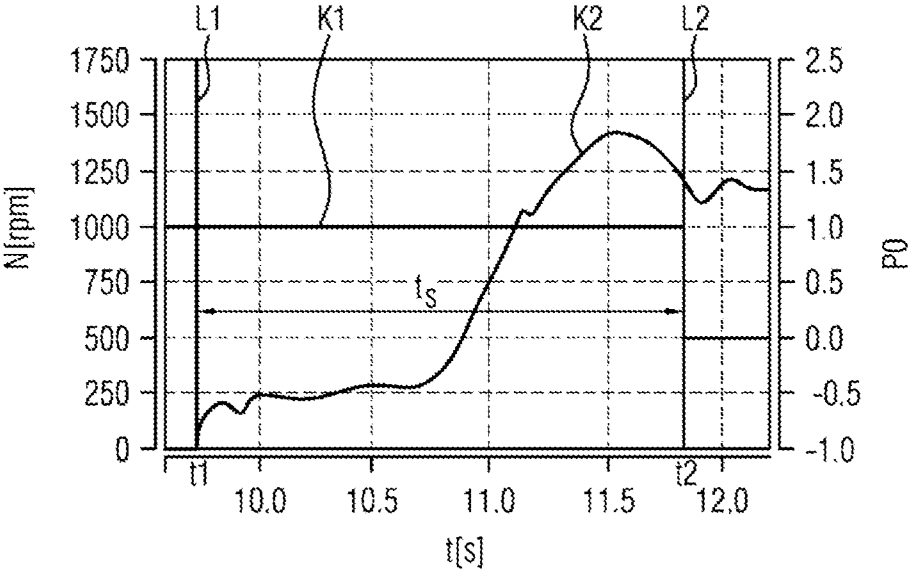
FIG. 2 shows a diagram illustrating the switching time of the oil pressure switch after a cold start of the internal combustion engine in the case of a fuel input in the oil of 1%.

FIG. 2 shows a diagram illustrating the switching time $t_s$ of the oil pressure switch after a cold start of the internal combustion engine in the case of a fuel input in the oil of 1%. The engine rotational speed N in revolutions per minute (rpm) is plotted upward on the left-hand side, the level PO of the output signal of the oil pressure switch is plotted upward on the right-hand side, and the time tin seconds is plotted from left to right. Within the diagram, line L1 denotes the time t1 of the starting operation of the engine, line L2 denotes the time t2 at which the oil pressure switch 2 outputs the switching signal, curve K1 denotes the level of the output signal of the oil pressure switch, and curve K2 denotes the course of the engine rotational speed N. It can be seen from FIG. 2 that the engine rotational speed N at which the oil pressure switch outputs the switching signal is approximately 1220 rpm, and that the switching time $t_s$ of the oil pressure switch, that is to say the duration between the starting operation of the engine and the outputting of the switching signal, is approximately 2.1 s.

Figure 3:
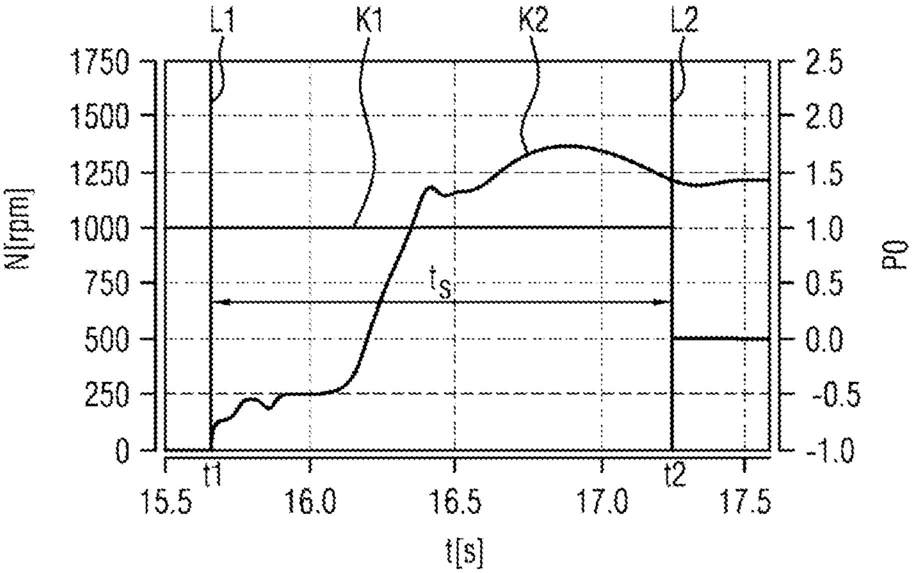
FIG. 3 shows a diagram illustrating the switching time of the oil pressure switch after a cold start of the internal combustion engine in the case of a fuel input in the oil of 10%.

FIG. 3 shows a diagram illustrating the switching time $t_s$ of the oil pressure switch after a cold start of the internal combustion engine in the case of a fuel input in the oil of 10%. The engine rotational speed N in revolutions per minute (rpm) is plotted upward on the left-hand side, the level PO of the output signal of the oil pressure switch is plotted upward on the right-hand side, and the time tin seconds is plotted from left to right. Within the diagram, line L1 denotes the time t1 of the starting operation of the engine, line L2 denotes the time t2 at which the oil pressure switch 2 outputs the switching signal, curve K1 denotes the level of the output signal of the oil pressure switch, and curve K2 denotes the course of the engine rotational speed N. It can be seen from FIG. 3 that the engine rotational speed N at which the oil pressure switch outputs the switching signal is approximately 1250 rpm, and that the switching time of the oil pressure switch, that is to say the duration between the starting operation of the engine and the outputting of the switching signal, is approximately 1.55 s.

Figure 4:
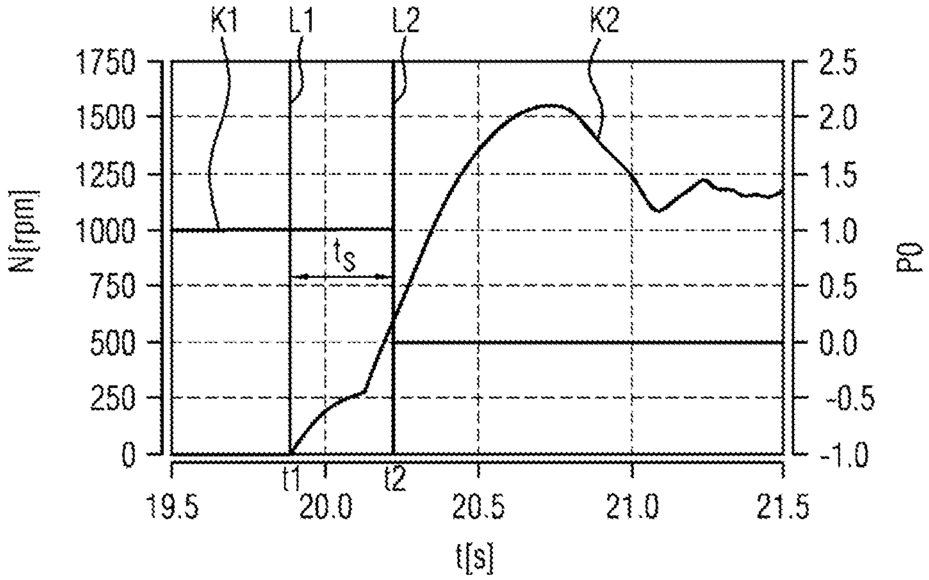
FIG. 4 shows a diagram illustrating the switching time of the oil pressure switch after a hot start of the internal combustion engine in the case of a fuel input in the oil of 1%.

FIG. 4 shows a diagram illustrating the switching time $t_s$ of the oil pressure switch after a subsequent or hot start of the internal combustion engine in the case of a fuel input in the oil of 1%. The engine rotational speed N in revolutions per minute (rpm) is plotted upward on the left-hand side, the level PO of the output signal of the oil pressure switch is plotted upward on the right-hand side, and the time tin seconds is plotted from left to right. Within the diagram, line L1 denotes the time t1 of the starting operation of the engine, line L2 denotes the time t2 at which the oil pressure switch 2 outputs the switching signal, curve K1 denotes the level of the output signal of the oil pressure switch, and curve K2 denotes the course of the engine rotational speed N. It can be seen from FIG. 4 that the engine rotational speed N at which the oil pressure switch outputs the switching signal is approximately 590 rpm, and that the switching time of the oil pressure switch, that is to say the duration between the starting operation of the engine and the outputting of the switching signal, is approximately 0.35 s.

Figure 5:
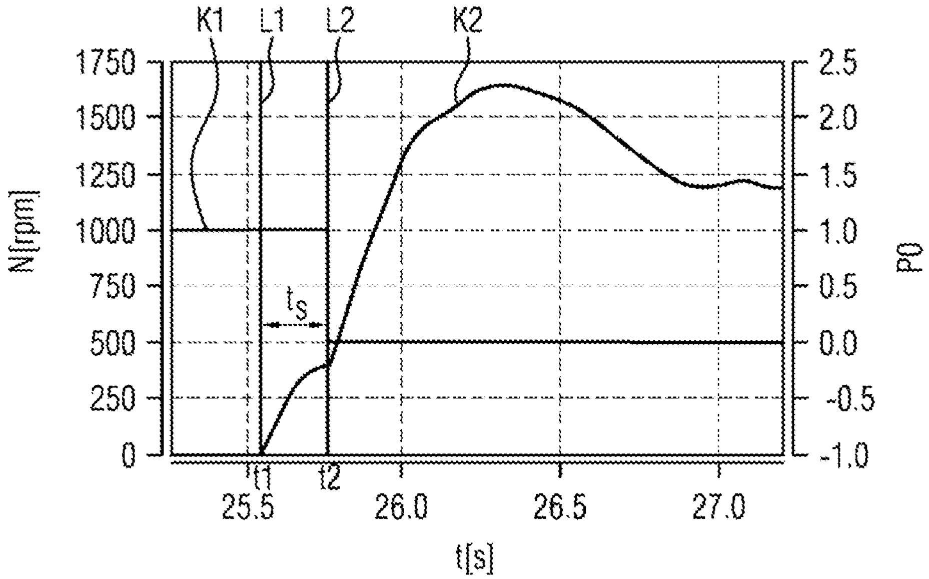
FIG. 5 shows a diagram illustrating the switching time of the oil pressure switch after a hot start of the internal combustion engine in the case of a fuel input in the oil of 10%.

FIG. 5 shows a diagram illustrating the switching time $t_s$ of the oil pressure switch after a subsequent or hot start of the internal combustion engine in the case of a fuel input in the oil of 10%. The engine rotational speed N in revolutions per minute (rpm) is plotted upward on the left-hand side, the level PO of the output signal of the oil pressure switch is plotted upward on the right-hand side, and the time tin seconds is plotted from left to right. Within the diagram, line L1 denotes the time t1 of the starting operation of the engine, line L2 denotes the time t2 at which the oil pressure switch 2 outputs the switching signal, curve K1 denotes the level of the switching signal, and curve K2 denotes the course of the engine rotational speed N. It can be seen from FIG. 5 that the engine rotational speed N at which the oil pressure switch outputs the switching signal is approximately 380 rpm, and that the switching time of the oil pressure switch, that is to say the duration between the starting operation of the engine and the outputting of the switching signal, is approximately 0.20 s.

If the acquired switching times are assigned to the start types (cold start or subsequent or hot start) at different engine starting temperatures, then an oil quality model can be empirically ascertained, which oil quality model is stored in the memory 4, and on the basis of which oil quality model conclusions regarding the engine oil quality can be drawn during the operation of the internal combustion engine based on the acquired switching times and the acquired engine temperatures.

Here, the determination of the oil quality is performed by a repeated measurement of the switching times and a subsequent evaluation using the stored oil quality model.

Advantages of the disclosure include ascertaining short-term engine oil quality information and long-term engine oil quality information. Here, the short-term engine oil quality information provides information regarding the short-term fuel input into the engine oil. The long-term engine oil quality information provides information regarding the effects of long-term oil aging.

Increasing fuel input into the engine oil takes place in the case of repeated cold starts without significant periods of driving operation when the engine has fully warmed up, that is to say in the case of successive driving of numerous short distances with a cold engine. Due to the input of fuel, the viscosity of the engine oil decreases dynamically. There is a tendency for continuously shorter switching times of the oil pressure switch to be measured over several measured engine starts. If the warmed-up engine operating state is reached during driving operation, then the fuel constituents are outgassed from the engine oil. This results in a very rapid increase in viscosity.

Superposed on the short-term behavior of the oil quality is the long-term reduction in viscosity due to aging of the engine oil. Multigrade oils are oils with additives and a specific basic viscosity. The additives ensure that the single-grade oil covers a range of viscosities. With increasing age, the oil assumes its basic viscosity.

Figure 6:
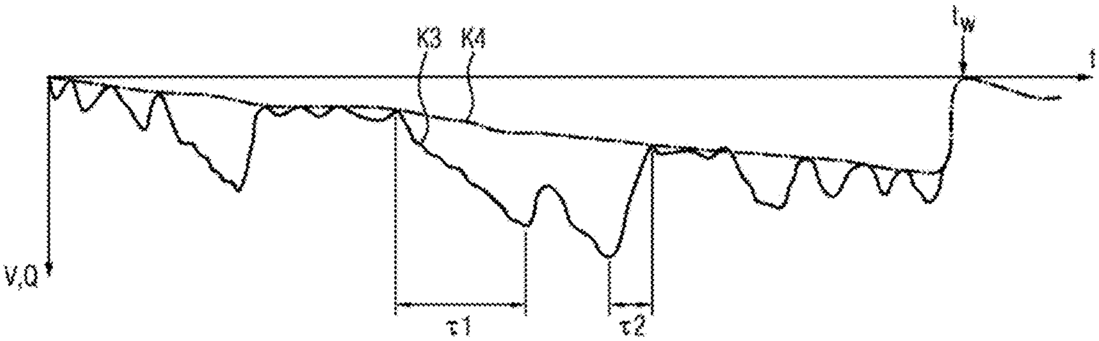
FIG. 6 shows a diagram in which short-term oil quality information and long-term oil quality information are explained.

FIG. 6 shows a diagram in which short-term engine oil quality information and long-term engine oil quality information are explained. In this diagram, a decreasing engine oil viscosity V and thus also a decreasing engine oil quality Q are plotted downward on the vertical axis, and the time t is plotted from left to right. The curve K3 illustrated in the diagram describes short-term engine oil quality information. The curve K4 illustrated in the diagram describes long-term engine oil quality information. The interval $\tau 1$ corresponds to an interval in which the engine has successively driven several short distances without reaching operating temperature. In this interval $\tau 1$, the fuel input in the oil increases. As a result, the engine oil quality Q and the engine oil viscosity V decrease. The interval $\tau 2$ corresponds to an interval in which driving operation with an engine at operating temperature is present. In this interval $\tau 2$, the fuel input in the engine oil decreases. The engine oil quality Q and the engine oil viscosity V thus increase. Also indicated in FIG. 6 is the time $t_w$ at which an oil change is due. This time is reached when the long-term engine oil quality information falls below a specified engine oil quality.

The oil quality information ascertained using the stored oil quality model can, according to some examples, be compared with information from one or more further models, the data of which are stored in the second memory 5 shown in FIG. 1. For example, these further models may correspond to a modeling of the fuel inputs in the engine oil based on the blow-by behavior and the outgassing when the engine operating temperature is reached.

If the engine configuration includes a controlled oil pump with settable pressure level, it is possible to ascertain the oil quality during driving operation by a targeted change of the oil pressure setpoint value. Here, switching is performed between high and low oil pressure levels. The engine oil quality is then determined from the delayed switching times of one or more oil pressure switches.

With the ascertained engine oil quality, recommendations for variable oil change intervals can be output. Warnings regarding excessively high proportions of fuel in the oil can also be shown on the display 6 during driving operation. A simplified oil level plausibility check can also be performed by a brief reduction in the viscosity of the engine oil. A warning regarding foaming of the engine oil by the crankshaft can also be shown on the display 6.

A number of implementations have been described. Nevertheless, it will be understood that various modifications may be made without departing from the spirit and scope of the disclosure. Accordingly, other implementations are within the scope of the following claims.

What is claimed is:

1. A method for determining engine oil quality of an internal combustion engine, the method comprising:

receiving, at an engine controller supported by the internal combustion engine, switching information of the internal combustion engine from an oil pressure switch;

determining, at the engine controller, switching times of the oil pressure switch based on the switching information after a starting operation of the internal combustion engine;

determining, at the engine controller, the engine oil quality of the internal combustion engine based on the switching times of the oil pressure switch; and displaying, at a display in communication with the engine controller, a warning message based on the determined engine oil quality;

wherein the switching time of the oil pressure switch is a period of time that elapses from the starting operation of the internal combustion engine until outputting of switching information by the oil pressure switch.

2. The method of claim 1, wherein the starting operation of the internal combustion engine is a cold start of the internal combustion engine.

3. The method of claim 1, wherein the starting operation of the internal combustion engine is a hot start of the internal combustion engine.

4. The method of claim 1, wherein the engine oil quality is dependent on an engine temperature prevailing upon the starting operation of the internal combustion engine.

5. The method of claim 1, wherein the engine oil quality is based on a stored oil quality model.

6. The method of claim 1, wherein evaluating the switching times of the oil pressure switch is repeated.

7. The method of claim 1, further comprising ascertaining short-term engine oil quality information.

8. The method of claim 1, further comprising ascertaining long-term engine oil quality information.

9. The method of claim 1, further comprising detecting changes in a viscosity of the engine oil.

10. The method of claim 1, further comprising comparing the determined oil quality information with a further model.

11. The method of claim 1, wherein the engine oil quality is determined during driving operation of the internal combustion engine using a targetedly effected change of an oil pressure setpoint value.

12. A device for determining engine oil quality of an internal combustion engine, the device comprising:

an oil pressure switch transmitting binary switching information; and an engine controller receiving the binary switching information, wherein after a starting operation of the internal combustion engine, when a specified pressure threshold is exceeded, the engine controller:

determines the switching times of the oil pressure switch based on the received binary switching information, determines the engine oil quality of the internal combustion engine based on the switching times of the oil pressure switch, and displaying, at a display in communication with the engine controller, a warning message based on the determined engine oil quality;

wherein the switching time of the oil pressure switch is a period of time that elapses from the starting operation of the internal combustion engine until outputting of switching information by the oil pressure switch.

13. The device of claim 12, wherein the starting operation of the internal combustion engine is a cold start of the internal combustion engine.

14. The device of claim 12, wherein the starting operation of the internal combustion engine is a hot start of the internal combustion engine.

15. The device of claim 12, wherein the engine oil quality is dependent on an engine temperature prevailing upon the starting operation of the internal combustion engine.

16. The device of claim 12, wherein the engine oil quality is based on a stored oil quality model.

17. The device of claim 12, wherein evaluating the switching times of the oil pressure switch is repeated.

18. The device of claim 12, wherein the engine controller determines the engine oil quality also by:

ascertaining short-term engine oil quality information.

19. The device of claim 12, wherein the engine controller determines the engine oil quality also by:

ascertaining long-term engine oil quality information.

20. The device of claim 12, wherein the engine controller determines the engine oil quality also by:

detecting changes in a viscosity of the engine oil.

* * * * *